United States Patent [19]

Miyazaki

[11] Patent Number: 5,457,726
[45] Date of Patent: Oct. 10, 1995

[54] ANALYZER FOR TOTAL REFLECTION FLUORESCENT X-RAY AND ITS CORRECTING METHOD

[75] Inventor: Kunihiro Miyazaki, Tokyo, Japan

[73] Assignee: Kabushiki Kaisha Toshiba, Kawasaki, Japan

[21] Appl. No.: 321,825

[22] Filed: Oct. 6, 1994

[30] Foreign Application Priority Data

Oct. 7, 1993 [JP] Japan ................................ 5-251796

[51] Int. Cl.$^6$ .............................................. G01N 23/223
[52] U.S. Cl. ................................ 378/45; 378/46; 378/48; 378/90
[58] Field of Search ......................... 378/45, 46, 48, 378/49, 50, 86, 88, 89, 90

[56] References Cited

U.S. PATENT DOCUMENTS

| 3,375,369 | 3/1968 | Goldman et al. | 378/46 X |
| 3,621,245 | 11/1971 | Clayton et al. | 378/46 |
| 4,169,228 | 9/1979 | Briska et al. | 378/50 X |
| 5,077,766 | 12/1991 | Schwenke et al. | 378/50 X |
| 5,128,545 | 7/1992 | Komi | 378/46 X |
| 5,220,591 | 6/1993 | Obsugi et al. | 378/45 |
| 5,249,216 | 9/1993 | Obsugi et al. | 378/46 |

FOREIGN PATENT DOCUMENTS 5-52777 3/1993 Japan.

*Primary Examiner*—David P. Porta
*Attorney, Agent, or Firm*—Finnegan, Henderson, Farabow, Garrett & Dunner

[57] ABSTRACT

A sample is mounted on a sample base. A detector is provided on the sample base, and detects a fluorescent X-ray generated from the sample, and a scattered X-ray of an incident X-ray when the sample is irradiated with the incident X-ray. A controller controls the sample base and an operation of the detector. The controller sequentially changes an incident angle of the incident X-ray to the sample so as to detect the fluorescent X-ray generated from the sample at each incident angle, and the scattered X-ray of the incident X-ray. Next, the controller obtains the relationship between the incident angle of the incident X-ray to the sample and a standard value obtained by standardizing intensity of the fluorescent X-ray by intensity of the scattered X-ray. Then, the controller corrects the incident angle of the incident X-ray to the sample based on the obtained relationship. Moreover, the controller corrects the positional relationship between an irradiation position of the incident X-ray to the sample and said detector based on the obtained relationship. In this case, the correction of the incident angle of the incident X-ray to said sample is made after ending the correction of the positional relationship.

11 Claims, 8 Drawing Sheets

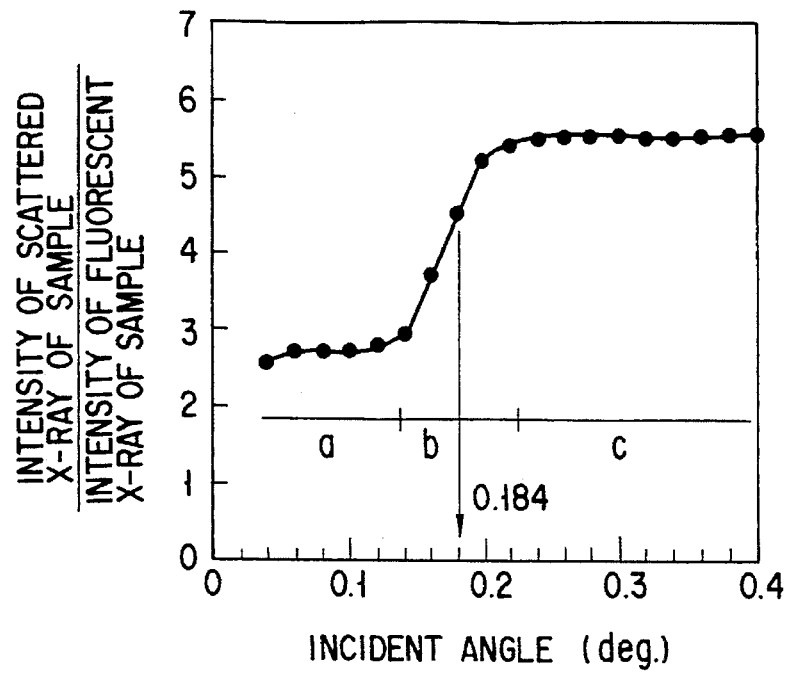
F I G. 9
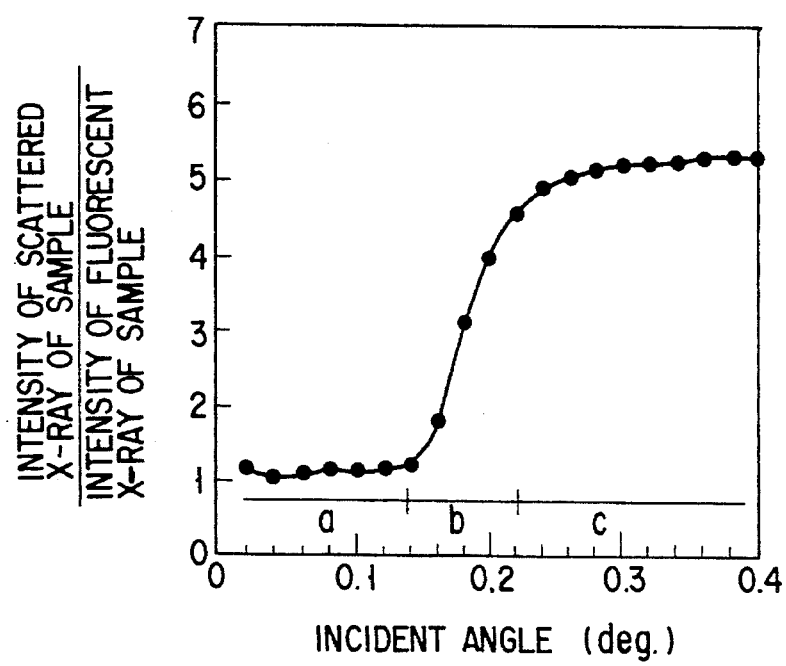
F I G. 10

5,457,726

ANALYZER FOR TOTAL REFLECTION FLUORESCENT X-RAY AND ITS CORRECTING METHOD

BACKGROUND OF THE INVENTION

1. Field of the Invention

The present invention relates to a correcting method of an analyzer for a total reflection fluorescent X-ray.

2. Description of the Related Art

An analyzer for a fluorescent X-ray using a phenomenon in which an X-ray irradiated to a sample at a small incident angle is totally reflected on a sample surface is applied to measure minor impurity materials on the sample surface, which is optically polished.

In the total reflection fluorescent X-ray analyzer, a primary X-ray emitted from an X-ray source is reflected on a surface of a sample, for example, a surface of a semiconductor wafer. At this time, a fluorescent X-ray emitted from a portion close to the surface of the wafer, that is, a secondary X-ray is detected by a secondary X-ray detector, whereby an inner surface distribution of minor impurity material adhered to the surface of the sample.

More specifically, if an optically smooth plane is irradiate with X-ray at a small incident angle, the X-ray is reflected conformably to the incident angle without being absorbed by the sample irradiated with X-ray. In other words, the X-ray is totally reflected. At this time, if there is minor impurity material on a portion close to the plane, the X-ray does not enter the sample deeply. Due to this, the fluorescent X-ray from the sample and a scattered X-ray can be prevented, and the fluorescent X-ray from the minor impurity material can be detected with high sensitivity.

Therefore, an S/N ratio (a ratio of a signal to noise) can be sufficiently detected.

Conventionally, there have been known two types of total reflection fluorescent X-ray analyzers, that is, a total reflection fluorescent X-ray analyzer having a detector for reflected wave, and a total reflection fluorescent X-ray analyzer having no detector for reflected wave.

(a) FIG. 1 shows a simply structured total reflection fluorescent X-ray analyzer having no detector for reflected wave. FIG. 2 is a view showing an incident ray and an X-ray generated from the sample.

A primary X ray 12' generated by an anticathode 11 is made monochromatic and densified, and inputted on a sample 14 (semiconductor wafer) at a predetermined incident angle.

In a case that the incident angle θ of the monochromatic incident X-ray 12 to the sample 14 is sufficiently small (smaller than a total reflection critical angle φ (φ<θ)), the fluorescent X-ray from the sample and the scattered X-ray can be almost ignored since the X-ray 12 is totally reflected as shown in FIG. 2, and a fluorescent X-ray 15 from impurity material 101 can be detected by a detector 16.

However, since this type of the total reflection fluorescent X-ray analyzer can not confirm the change of intensity of a reflected wave 17, there is a disadvantage in that the incident angle θ of the X-ray cannot be correctly obtained. In other words, according to this type of the total reflection fluorescent X-ray analyzer, since the total reflection critical angle φ of the incident X-ray is obtained by measuring the intensity of the fluorescent X-ray 15, the correct the total reflection critical angle φ cannot be obtained, an error of the incident angle θ of the X-ray is large, and the analysis of the sample cannot be correctly performed.

In a case that the incident angle θ of the incident x-ray 12 to the sample 14 is larger than the total reflection critical angle φ (θ>φ), the incident X-ray 12 enters the sample 14, and a large amount of the fluorescent X-ray and scattered X-ray 18 are generated from the inside of the sample 14. Due to this, the S/N ratio extremely worsens.

(b) FIG. 4 shows the total reflection fluorescent X-ray analyzer having a detector for reflected wave.

The primary X ray 12' generated by the anticathode 11 is made monochromatic, and inputted on the sample 14 at an incident angle θ1. The reflected wave 17, which is reflected on the sample 14, is detected by a detector 19 for reflected wave. Therefore, this type of the total reflection fluorescent X-ray analyzer can correctly obtain the incident angle θ1 of the X-ray.

However, for changing the incident angle θ1 of the incident X-ray 12, there is needed a mechanism in which the sample 14 is inclined and a reflected angle θ to the sample 14 of a detector 19 for reflected wave (or an angle θ3 of the reflected X-ray to the incident X-ray) is adjusted with extremely high accuracy.

Therefore, there are disadvantages in which a number of parts is increased and the structure becomes complicated in order to realize the above-mentioned adjusting mechanism.

Moreover, the above type of the total reflection fluorescent X-ray analyzer can correct the geometric positional relationship among the anticathode 11, a spectrometer 13, the sample 14, and the detector 19 for reflected wave. However, the correction of the detector 16 for fluorescent X-ray and that of an irradiation position 20 of the X-ray cannot be performed.

FIG. 5 shows the relationship between the incident angle of the X-ray and the fluorescent X-ray in intensity in a case that the positional relationship between the irradiation position of the X-ray and the detector for fluorescent X-ray is correct. FIG. 6 shows the relationship between the incident angle of the X-ray and the fluorescent X-ray in intensity in a case that the positional relationship between the irradiation position of the X-ray and the detector for fluorescent X-ray is incorrect.

In other words, according to the conventional total reflection fluorescent X-ray analyzer, as shown in FIGS. 5 and 6, the distribution of intensity of the fluorescent X-ray to the incident angle shows the same curvature even if the positional relationship between the irradiation position of the X-ray and the detector for the fluorescent x-ray is shifted. Due to this, the shift of the positional relationship between the irradiation position of the X-ray and the detector for the fluorescent X-ray cannot be detected.

As mentioned above, there were conventionally two types of total reflection fluorescent X-ray analyzers, that is, a total reflection fluorescent X-ray analyzer having a detector for reflected wave, and a total reflection fluorescent X-ray analyzer having no detector for reflected wave. However, in both types of the total reflection fluorescent X-ray analyzers, there are disadvantages in which the incident angle of the X-ray cannot be accurately corrected with a simple mechanism and the shift of the positional relationship between the irradiation position of the X-ray and the detector for the fluorescent X-ray cannot be corrected.

SUMMARY OF THE INVENTION

The present invention has been made to solve the above disadvantages, and its object is to provide a total reflection fluorescent X-ray analyzer having the following features:
 (a) the shift of the incident angle of the X-ray can be accurately corrected with a simple mechanism;
 (b) the shift of the positional relationship between the irradiation position of the x-ray and the detector for the fluorescent X-ray can be corrected; and
 (c) minor impurity material on the surface of the sample can be correctly measured by obtaining the above features (a) and (b).

In order to attain the above object, there is provided a total reflection fluorescent X-ray analyzer comprising a sample base for mounting a sample thereon; a detector, provided on the sample base, for detecting a fluorescent X-ray generated from the sample, and a scattered X-ray of an incident X-ray when the sample is irradiated with the incident X-ray; and a controller for controlling the sample base and an operation of the detector; the controller comprising first means for sequentially changing an incident angle of the incident X-ray to the sample so as to detect the fluorescent X-ray generated from the sample at each incident angle, and the scattered X-ray of the incident X-ray; second means for obtaining the relationship between the incident angle of the incident X-ray to the sample and a standard value obtained by standardizing intensity of the fluorescent X-ray by intensity of the scattered X-ray; third means for correcting the incident angle of the incident X-ray to the sample based on the obtained relationship.

The first means of the controller adjust an inclination of the sample to sequentially change the incident angle of the incident X-ray to the sample.

The controller further comprises fourth means for correcting the positional relationship between an irradiation position of the incident X-ray to the sample and the detector based on the obtained relationship, and the third means of the controller corrects an incident angle of the incident X-ray to the sample after ending the correction of the positional relationship.

The second means of the controller adjusts up and down positions of the sample base based on the obtained relationship so as to correct the positional relationship.

The second means of the controller obtains the standard value by dividing intensity of the scattered X-ray by intensity of the fluorescent X-ray.

The third means of the controller obtains a total reflection critical angle of the incident X-ray based on the obtained relationship, and corrects the incident angle of the incident X-ray to the sample based on the total reflection critical angle.

The controller further comprises fifth means for analyzing the sample after correcting the incident angle of the incident X-ray to the sample.

Moreover, according to the present invention, there is provided a method for analyzing a total reflection fluorescent x-ray comprising the steps of sequentially changing an incident angle of an incident x-ray to a sample to detect a fluorescent X-ray generated from the sample at each incident angle, and a scattered X-ray of the incident X-ray; obtaining the relationship between the incident angle of the incident X-ray to the sample and a standard value obtained by standardizing intensity of the fluorescent X-ray by intensity of the scattered X-ray; and correcting a shift of the incident angle of the incident x-ray to the sample, and a shift of the irradiation position of the incident X-ray based on the obtained relationship, respectively.

The shift of the incident angle of the incident X-ray to the sample is corrected after correcting the shift of the irradiation position of the incident X-ray.

The standard value is obtained by dividing intensity of the scattered X-ray by intensity of the fluorescent X-ray.

The shift of the incident angle of the incident X-ray to the sample by obtaining a total reflection critical angle of the incident X-ray based on the obtained relationship, and obtaining a correct incident angle based on the total reflection critical angle.

Additional objects and advantages of the invention will be set forth in the description which follows, and in part will be obvious from the description, or may be learned by practice of the invention. The objects and advantages of the invention may be realized and obtained by means of the instrutmentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 9 is a view showing the relationship between an incident angle of an X-ray and a standard value in a case that silicon is used as a sample;

FIG. 10 is a view showing the relationship between an incident angle of an X-ray and a standard value in a case that silicon oxide is used as a sample;

DETAILED DESCRIPTION OF THE PREFERRED EMBODIMENTS

A total reflection fluorescent X-ray analyzer of the present invention will be explained with reference to the drawings.

Figure 7:
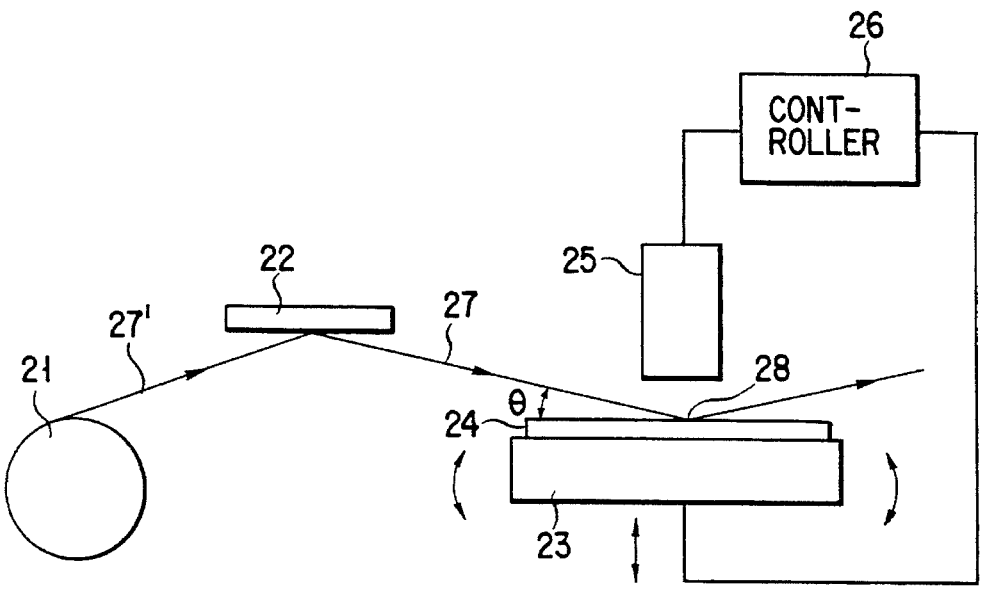
FIG. 7 is a view showing a total reflection fluorescent X-ray analyzer of the present invention.
Figure 2:
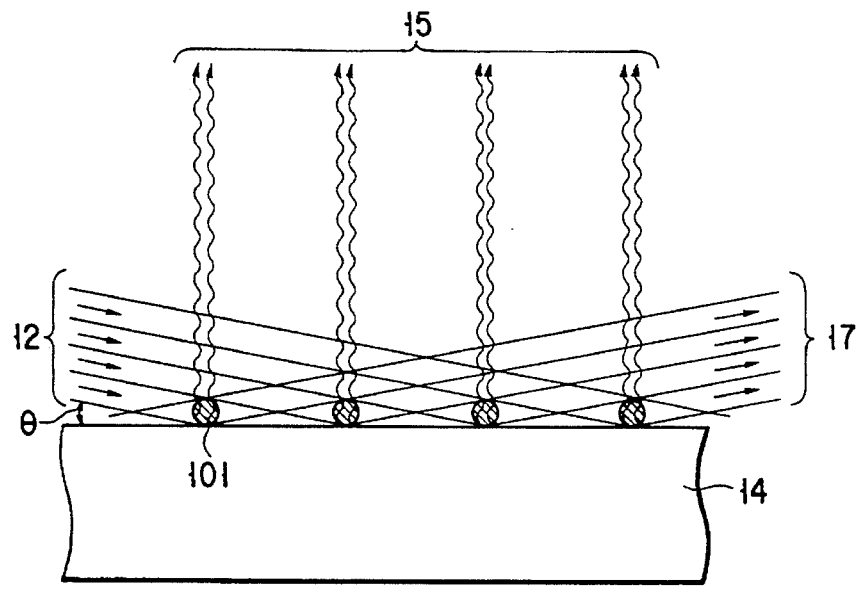
FIG. 2 is a view showing an incident X-ray and a fluorescent X-ray generated from minor impurity material.
Figure 3:
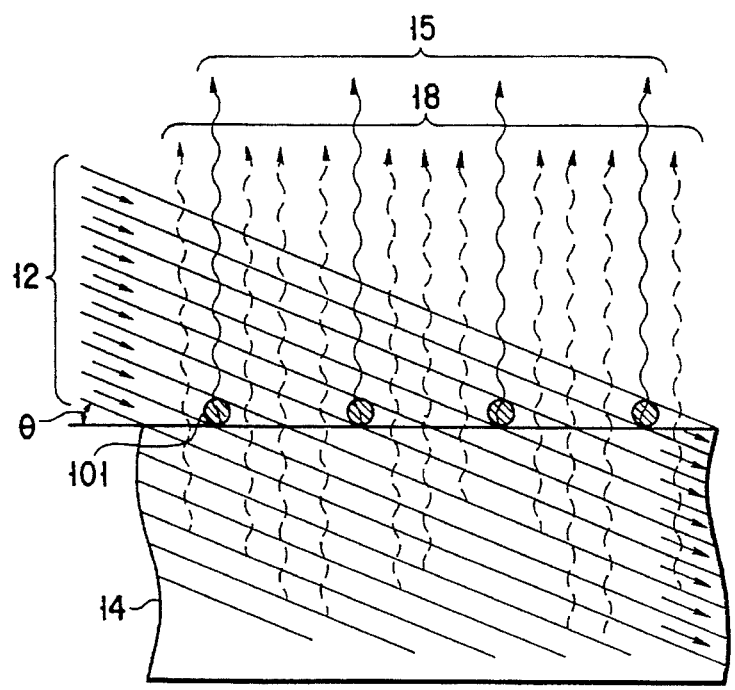
FIG. 3 is a view showing an incident X-ray, a fluorescent X-ray generated from a sample, and a scattered X-ray.
Figure 5:
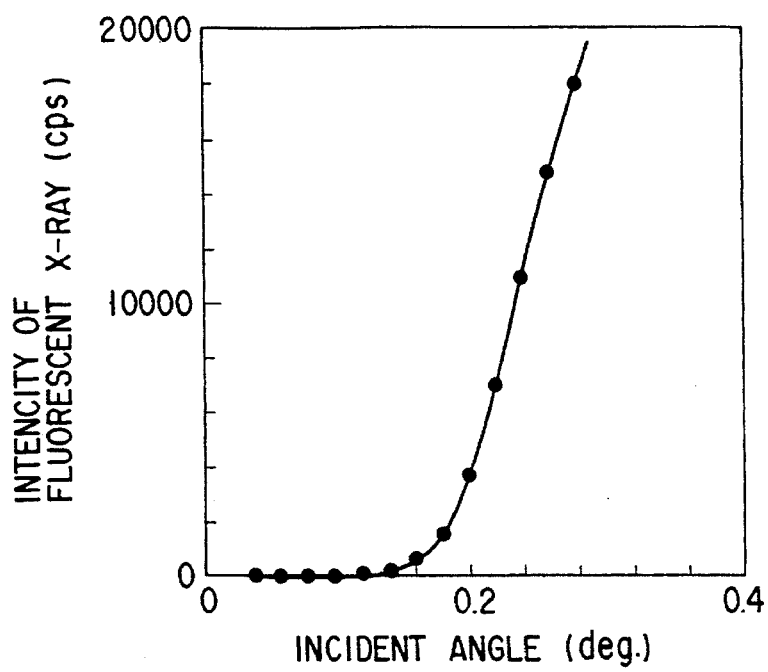
FIG. 5 is a view showing the relationship between an incident angle of the X-ray and a fluorescent X-ray in intensity.
Figure 6:
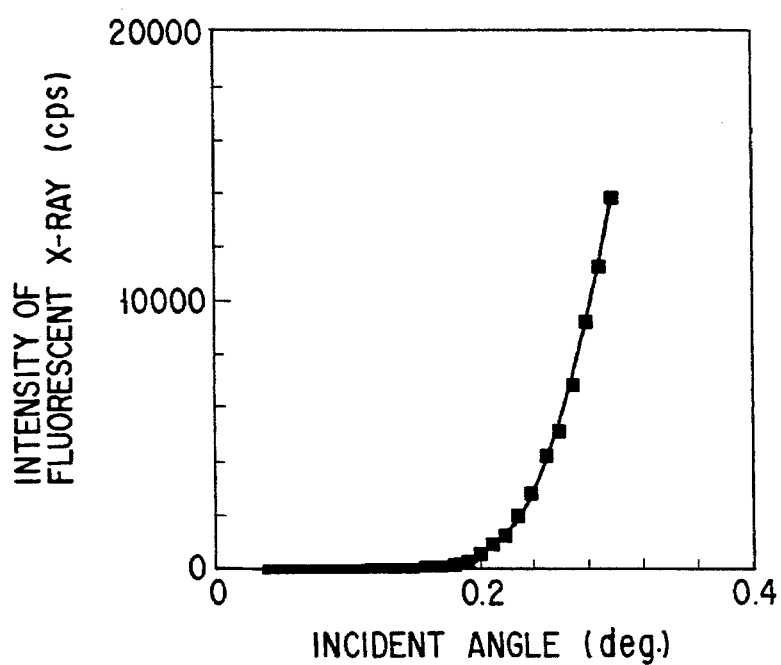
FIG. 6 is a view showing the relationship between an incident angle of the X-ray and a fluorescent X-ray in intensity.

FIG. 7 shows the total reflection fluorescent X-ray analyzer of the present invention.

Reference numeral 21 is an anticathode as a supply source of an X-ray, 22: a spectrometer, 23: a sample base, 24: a sample, 25: a detector, and 26: a controller.

This total reflection fluorescent X-ray analyzer has no detector for reflected wave, and the number of parts is small, and the structure is simple.

A primary X ray 27' generated by the anticathode 21 is made monochromatic by the spectrometer 22, and inputted on the sample 24 at a predetermined incident angle θ.

In a case that the incident angle θ of a monochromatic incident x-ray 27 to the sample 14 is sufficiently small (smaller than a total reflection critical angle φ (θ<φ)), the incident X-ray 27 is totally reflected.

The fluorescent X-ray of the sample 24 generated at an irradiation position 28 of the X-ray and a scattered x-ray are detected by the detector 25. The incident angle θ of the incident X-ray 27 to the sample 24 can be changed by inclining the sample base 23.

The controller 26 obtains the relationship between the incident angle of the incident X-ray 27 and a standard value, which is obtained by standardizing intensity of the fluorescent X-ray by intensity of the scattered X-ray (intensity of scattered X-ray/intensity of fluorescent X-ray). Moreover, the controller determines a total reflection critical angle φ and corrects the incident angle of the x-ray to the sample. Thereafter, the controller analyzes the sample.

Also, the controller 26 adjusts the height of the sample base 23 of the detector 25, whereby the positional relationship between the irradiation position of the X-ray and the detector for reflected detector can be corrected.

Figure 8:
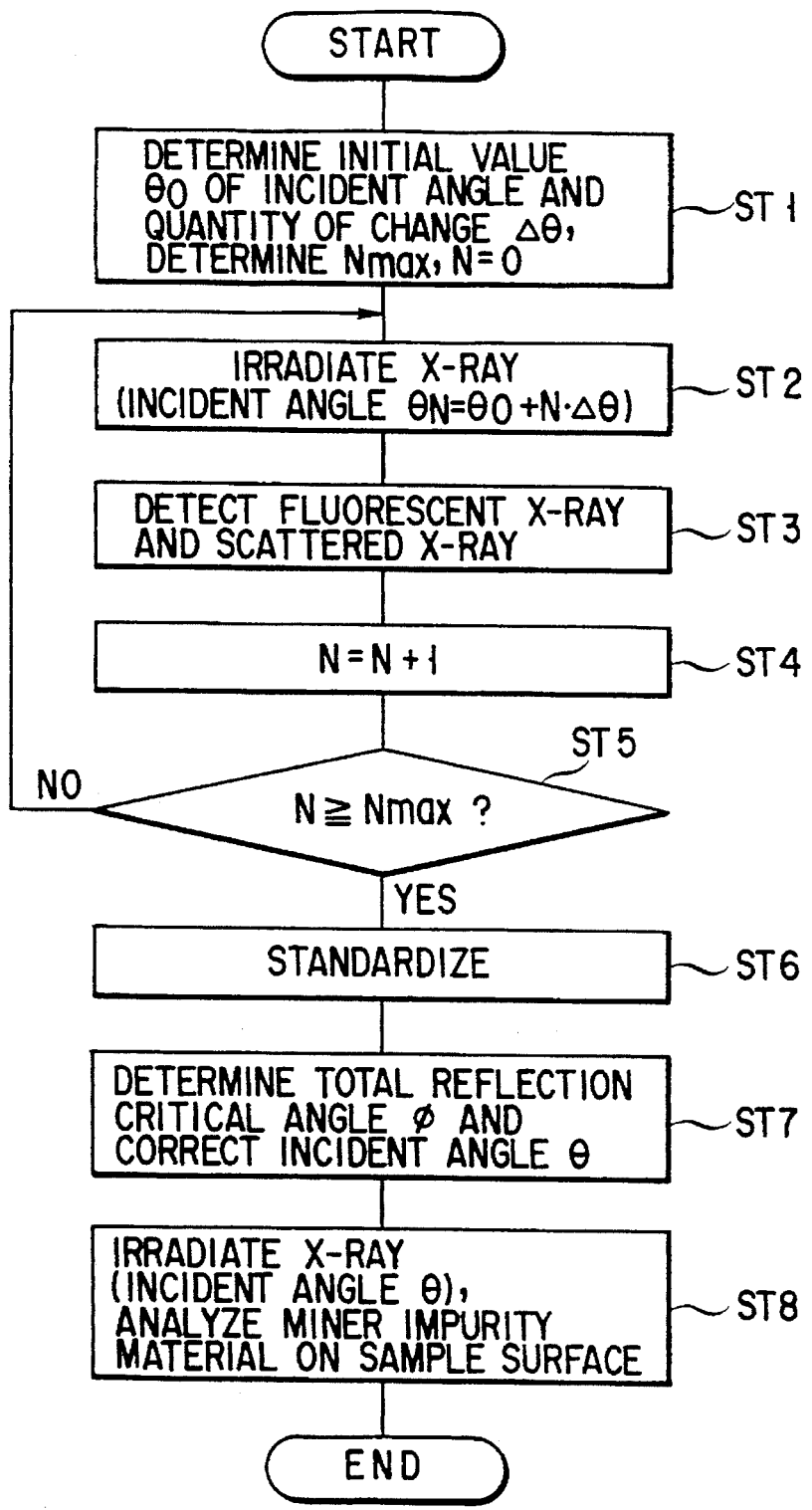
FIG. 8 is a flow chart showing one example of an operation of the apparatus of FIG. 7.

The following will explain an operation (correcting method) of the total reflection fluorescent X-ray analyzer of the present invention with reference to FIG. 8.

First of all, data for obtaining the total reflection critical angle φ is collected.

More specifically, the sample 24 (for example, semiconductor wafer) is irradiated with the incident X-ray 27. The fluorescent X-ray of the sample generated from the sample by the irradiation of the incident X-ray 27 and the scattered X-ray are detected by the detector 25. Then, the inclination of the sample base 23 and the incident angle θ of the incident X-ray 27 are changed. Thereafter, the fluorescent X-ray of the sample and the scattered X-ray are detected by the detector 25. Such a detection of the fluorescent X-ray of the sample and the scattered X-ray as changing the incident angle θ is repeated a plurality of times (steps ST1 to ST5).

The above data collection is performed in accordance with the following program so as to simply collect data for a short period of time.

First of all, an initial value $θ_0$ of the incident angle of the X-ray, quantity of change→θ and quantity of data Nmax are determined (Step ST1).

Next, the sample 24 is irradiated with the X-ray at the incident angle $θ_0$, and the fluorescent X-ray of the sample 24 and the scattered X-ray are detected. Next, the sample 24 is irradiated with the X-ray at the incident angle $θ_0+Δθ$, and the fluorescent X-ray of the sample 24 and the scattered X-ray are detected. Similarly, the sample 24 is irradiated with the X-ray at the incident angle $θ_0+N.Δθ$, and the fluorescent X-ray of the sample 24 and the scattered X-ray are detected.

In this case, N (natural number)<$N_{max}$, and there is no need that the correct initial value θ is obtained (steps ST2 to ST5).

Next, intensity of the fluorescent X-ray of the sample 24 at each of incident angles $θ_0$, $θ_0+Δθ$, ... $θ_0+N.Δθ$ is standardized by intensity of the scattered X-ray. In other words, the value (standard value), is obtained by dividing intensity of the scattered X-ray by intensity of the fluorescent X-ray of the sample 24 (step ST6).

The total reflection critical angle φ is obtained from the relationship between the incident angle θ of the X-ray and the standard value.

More specifically, it is assumed that the total reflection critical angle φ obtained by the above step conforms to a total reflection critical angle (0.184° if silicon is used), which is obtained by an ideal curve. Then, the incident angle θ of the X-ray in analyzing the minor impurity material on the surface of the sample 24 is determined based on the total reflection critical angle φ, and the correction of the incident angle is performed (step ST7).

Thereafter, the sample 24 is irradiated with the X-ray at the incident angle θ, the minor impurity material on the surface of the sample 24 is analyzed (step ST8).

The following will explain the steps of determining the incident angle θ of the X-ray in obtaining the total reflection critical angle φ, and analyzing the minor impurity material on the surface of the sample 24 with reference to the specific example.

FIG. 9 shows the relationship between the incident angle θ of the X-ray and the standard value, which is obtained by standardizing intensity of the fluorescent X-ray by intensity of the scattered X-ray, in a case that silicon (Si) is used as a sample. FIG. 10 shows the relationship between the incident angle θ of the X-ray and the standard value, which is obtained by standardizing intensity of the fluorescent X-ray by intensity of the scattered X-ray, in a case that silicon oxide ($SiO_2$) is used as a sample.

As shown in FIGS. 9 and 10, in a total reflection area a where the X-ray is totally reflected and an area out of total reflection c where the X-ray enters a substrate, the standard value, which is obtained by standardizing intensity of the fluorescent X-ray by intensity of the scattered X-ray, is unchanged without depending on the incident angle of the X-ray.

On the other hand, a mixed area b where an X-ray component, which is totally reflected, and an X-ray component, which enters the substrate, are contained, intensity of the fluorescent x-ray and that of the scattered X-ray are changed. Due to this, the standard value is changed by the rate of intensity of the fluorescent X-ray and that of the scattered X-ray.

Therefore, it can be understood that the total reflection critical angle φ exists in the mixed area b.

The following will explain the reason why the mixed area b exists between the total reflection area a and the area c out of the total reflection without changing from the total reflection area a to the area c out of the total reflection immediately.

Figure 11:
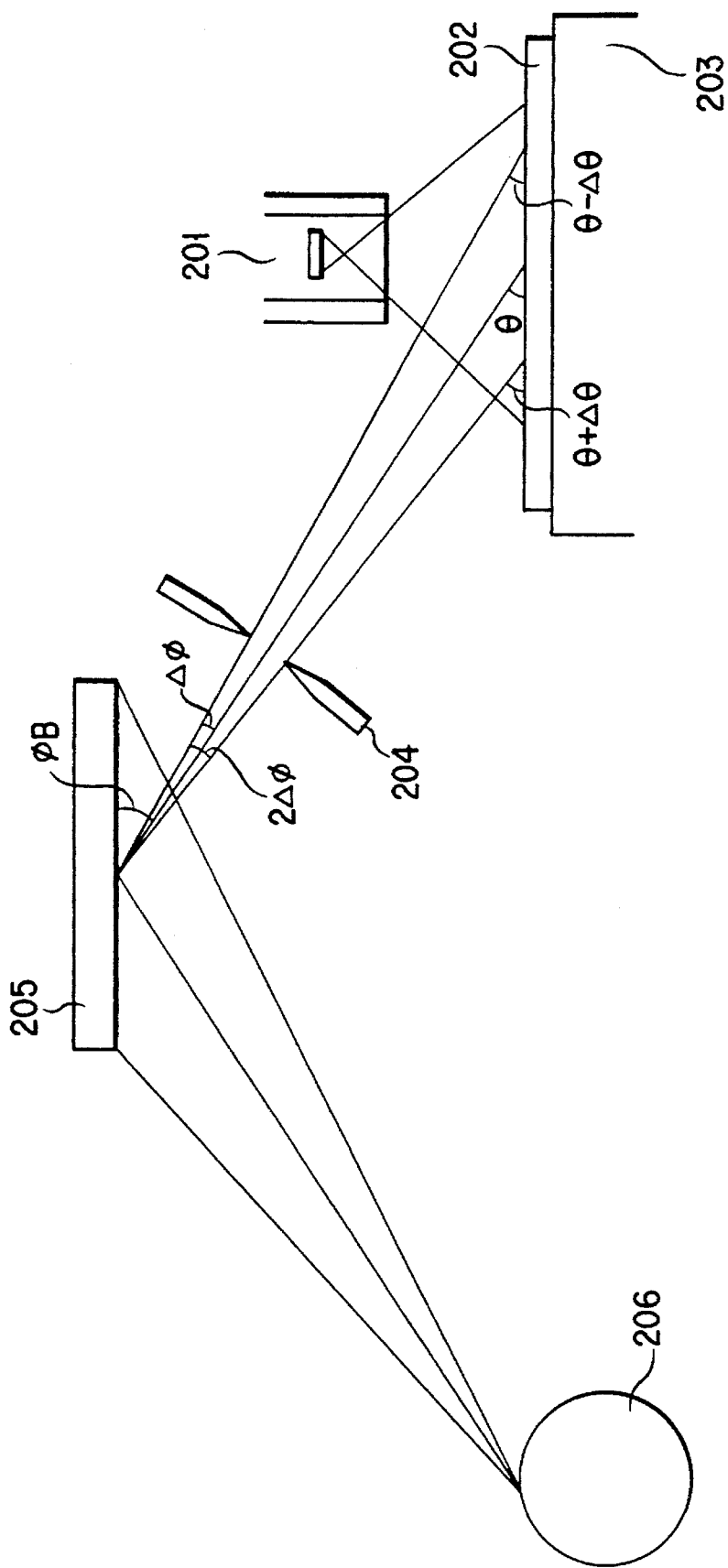
FIG. 11 is a view showing the relationship between a divergent angle $2\Delta\phi$ and an incident angle $\theta \pm \Delta\theta$ to a sample.

FIG. 11 shows the relationship between a divergent angle 2Δφ of the X-ray in a spectrometer 205 and the incident angle θ of the X-ray to a sample 202.

In a case that the divergent angle 2Δφ of the X-ray in the spectrometer 205, a wavelength of the X-ray with which the sample 202 is irradiated can be expressed under a Bragg condition as follows.

$$2d.\sin(φ_B±Δφ)=n(λ_B±Δλ)(n=1,2,3,\ldots) \quad [1]$$

wherein d is a surface distance of the spectrometer 205, and λ is a wavelength of the X-ray.

Moreover, the total reflection critical angle φ critical can be expressed as follows:

$$φcritical=\{(5.4×10^{10}.z.ρ.λ^2)/A\}^{1/2} \quad [2]$$

wherein A is a mass number of sample 202, Z is an atomic number, ρ is density, λ is a wavelengh of the X-ray.

In a case that a silicon wafer is used as a sample, A=28.09, Z=14, ρ=2.33 g/cm³.

Therefore, when the divergent angle is 2Δφ, the variation of the total reflection critical angle to the sample can be expressed as follows:

$$(\theta \pm \Delta\theta)\text{critical} = \{(5.4 \times 10^{10} \cdot z \cdot \rho \cdot (\lambda_B \pm \Delta\lambda))/A\}^{1/2} \quad [3]$$

wherein n=1 in equation [1].

In other words, the mixed area b shows the variation of the total reflection critical angle φ, and means the variation exists in the range of ±Δθ.

Therefore, if the divergent angle 2Δφ increases, the mixed area b (±Δθ) becomes wider.

As mentioned above, the divergent angle 2Δφ of the X-ray can be obtained from the width of the mixed area b, and the total reflection critical angle φ is determined to be an intermediate value between the minimum value of the mixed area b and the maximum value thereof.

The divergent angle 2Δφ is changed, depending on a window width of the detector 20, or the positional relationship among a target 206, the spectrometer 205, a slit 204, and the sample 202, or energy resolution of the spectrometer 205.

However, according to the above method, the total reflection critical angle φ can be correctly and readily obtained. Due to this, even in a case that a plurality of samples are analyzed, analysis of each sample can be performed as the incident angle θ to the sample can be maintained to be constant.

Moreover, in a case that the radiation range of the X-ray to the sample is wider than the range of the field of view of a detector 201, the divergent angle can be obtained in the range of the field of view of the detector.

As mentioned above, according to the total reflection fluorescent X-ray analyzer of the present invention and its correcting method, even in the simple structure having no detector for reflected wave, the total reflection area a and the area c out of the total reflection can be discriminated, and the correct total reflection critical angle φ can be obtained.

Moreover, in a case that the X-ray having energy of 9.67 KeV is used, the critical angle of silicon is about 0.184°. Judging from FIG. 9, an incident angle error $E_1$ is about ±0.005°, in a case when the incident angle of the X-ray is obtained by the total reflection fluorescent X-ray analyzer of the present invention.

An incident angle error $E_2$ is about ±0.002° in a case when the incident angle of the X-ray is obtained by the conventional total reflection fluorescent X-ray analyzer described in the item (a) of the prior art. The incident angle error becomes worse than the present invention.

Figure 12:
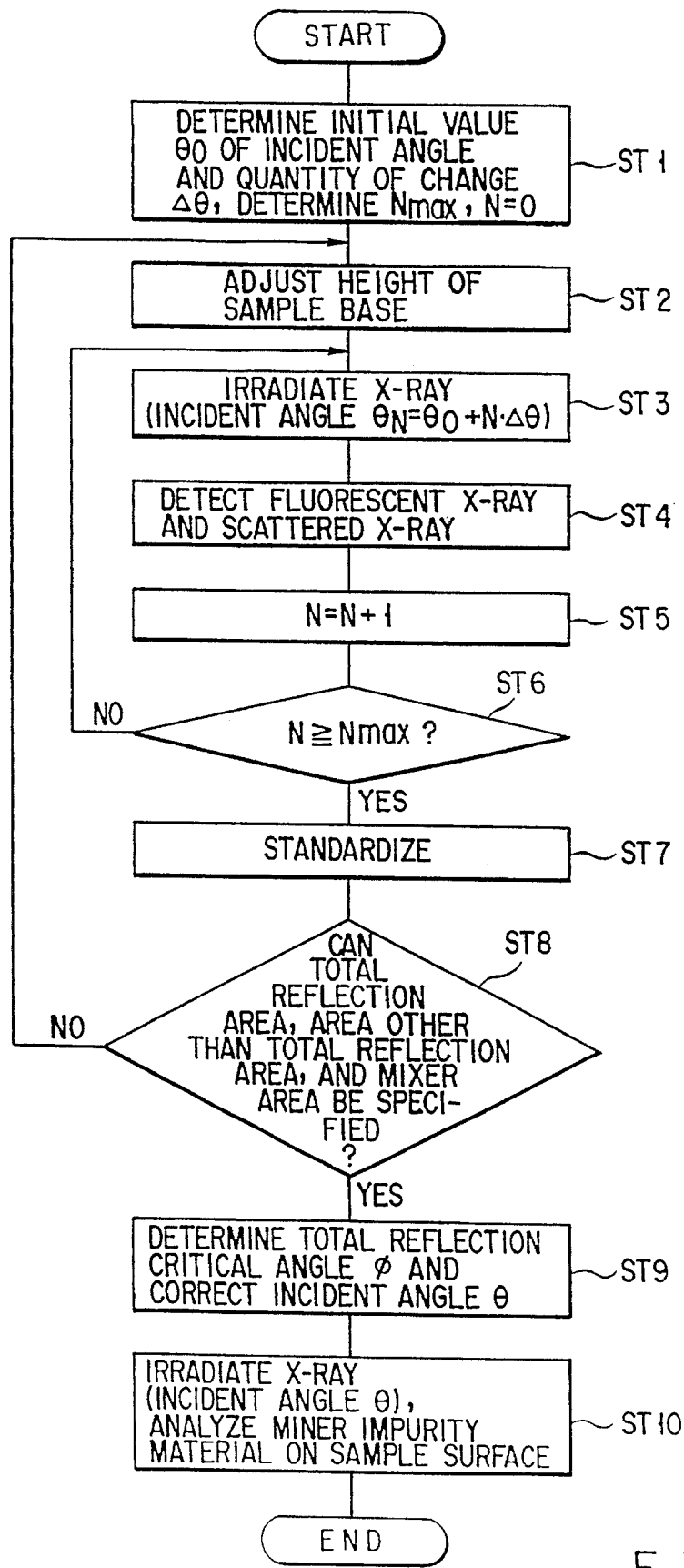
FIG. 12 is a flow chart showing the other example of the operation of the analyzer of FIG. 7.

The following will explain an operation (correction) of the total reflection fluorescent X-ray analyzer in correcting the positional relationship between the irradiation position of the X-ray and the fluorescent X-ray detector with reference to FIG. 12.

First of all, the height (up and down positions) of the sample base is adjusted to determine the positional relationship between the irradiation position of the X-ray and the fluorescent X-ray detector (step ST2).

Next, the sample (for example, semiconductor wafer) is irradiated with the X-ray. The fluorescent X-ray, which is generated from the sample by the irradiation of the X-ray, and the scattered X-ray are detected by the detector.

Then, the inclination of the sample base 23 is adjusted, and the incident angle of the incident X-ray is changed.

Thereafter, the fluorescent X-ray of the sample and the scattered X-ray are detected by the detector. Such a detection of the fluorescent X-ray of the sample and the scattered X-ray as changing the incident angle is repeated a plurality of times (steps ST3 to ST6).

Next, intensity of the fluorescent X-ray of the sample at each incident angle is standardized by intensity of the scattered X-ray. In other words, intensity of the scattered X-ray is divided by intensity of the fluorescent X-ray of the sample to obtain the value (standard value) (step ST7).

Also, in the graph showing the relationship between the incident angle of the standard value, it is determined whether or not the total reflection area a, the area c out of the total reflection, and the mixed area b can be correctly specified (step ST8).

In a case that the respective areas a, b, c can be correctly specified, the positional relationship between the irradiation position of the X-ray and the fluorescent X-ray detector is correct. Therefore, the total reflection critical angle φ and the divergent angle 2Δφ of the incident X-ray are determined, and the correction of the incident angle θ is performed (step ST9).

Thereafter, the sample is irradiated with the X-ray at the incident angle θ, and the minor impurity material on the surface of the sample is analyzed.

Figure 13:
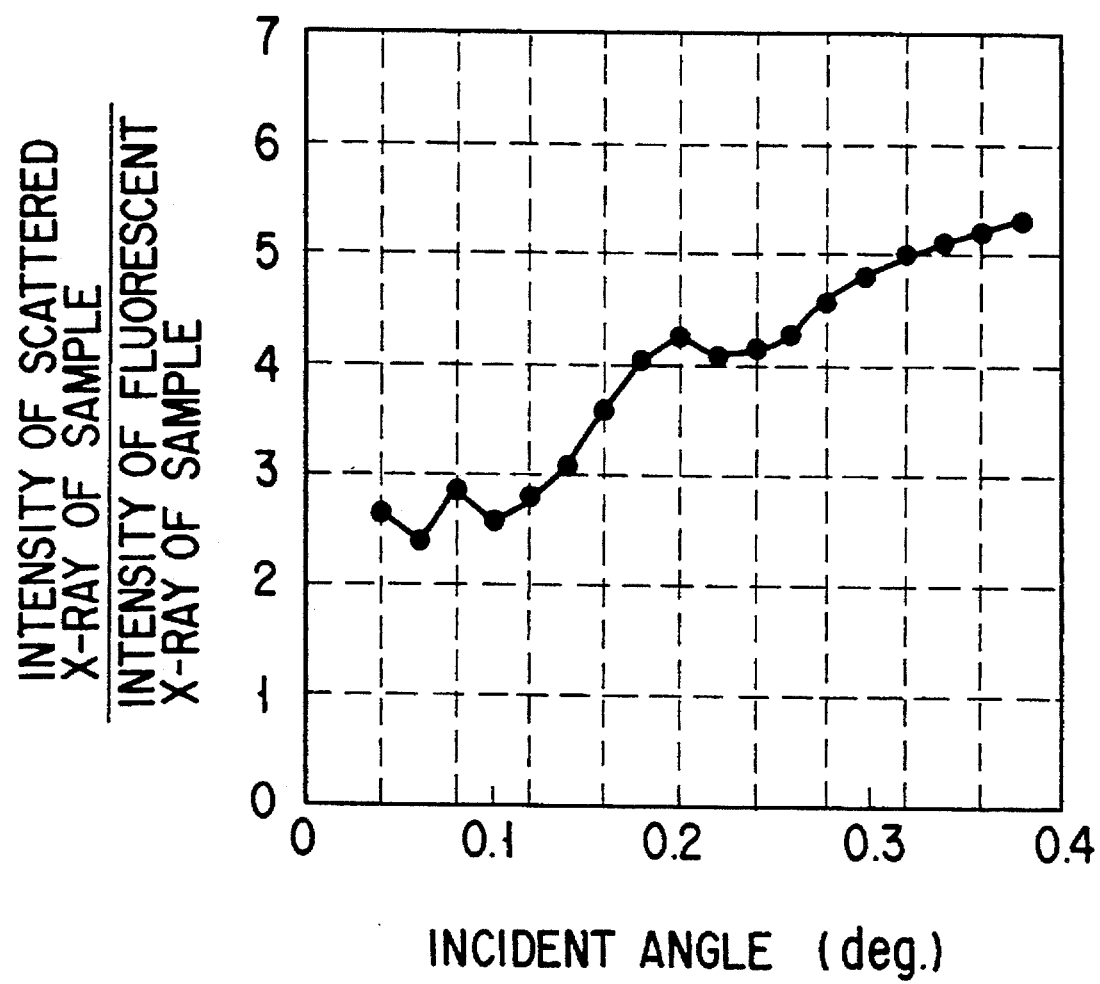
FIG. 13 is a view showing the relationship between an incident angle of an X-ray and a standard value.

On the other hand, as shown in FIG. 13, In a case that the respective areas a, b, c cannot be correctly specified, the positional relationship between the irradiation position of the X-ray and the fluorescent X-ray detector is incorrect. Due to this, the height (up and down positions) of the sample base is adjusted again, and the positional relationship between the irradiation position of the X-ray and the fluorescent X-ray detector is determined again.

Figure 1:
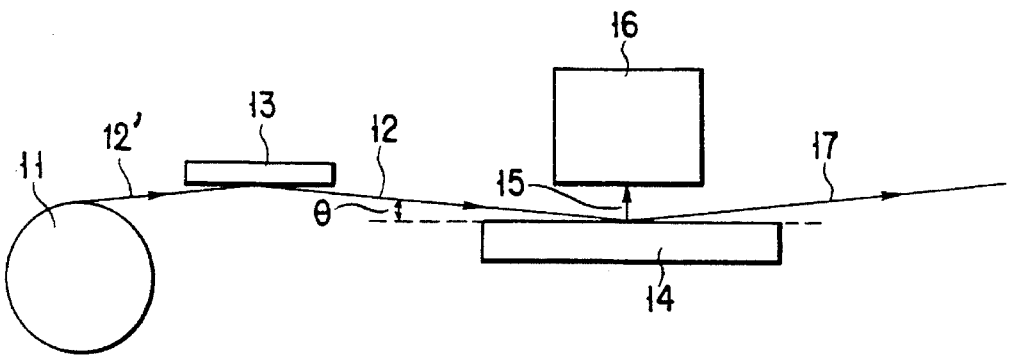
FIG. 1 is a view showing a conventional total reflection fluorescent X-ray analyzer.
Figure 4:
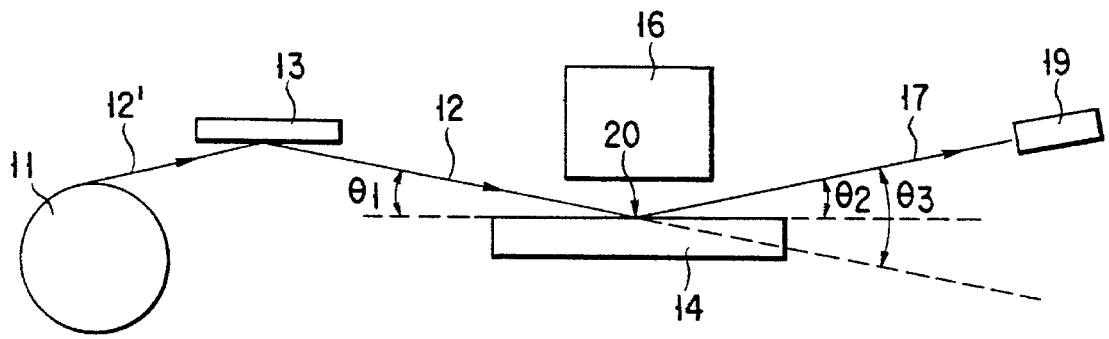
FIG. 4 is a view showing a conventional total reflection fluorescent X-ray analyzer.

As mentioned above, for example, according to the total reflection fluorescent X-ray analyzer having the detector for reflected wave of FIG. 4, the positional relationship between the irradiation position of the X-ray and the fluorescent X-ray detector cannot be corrected. In contrast, according to the total reflection fluorescent X-ray analyzer having the detector for reflected wave of the present invention, the positional relationship between the irradiation position of the X-ray and the fluorescent X-ray detector cannot be corrected.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A total reflection fluorescent X-ray analyzer comprising:

a sample base for mounting a sample thereon;

a detector, provided on said sample base, for detecting a fluorescent X-ray generated from the sample, and a scattered X-ray of an incident X-ray when said sample is irradiated with said incident X-ray; and a controller for controlling said sample base and an operation of said detector;

said controller comprising:

first means for sequentially changing an incident angle of said incident X-ray to said sample so as to detect the fluorescent X-ray generated from said sample at each incident angle, and the scattered X-ray of said incident X-ray;

second means for obtaining the relationship between the incident angle of said incident X-ray to said sample and a standard value obtained by standardizing intensity of said fluorescent X-ray by intensity of said scattered X-ray;

third means for correcting the incident angle of said incident X-ray to said sample based on said obtained relationship.

2. The total reflection fluorescent X-ray analyzer according to claim 1, wherein said first means of said controller adjust an inclination of said sample to sequentially change the incident angle of said incident X-ray to the sample.

3. The total reflection fluorescent X-ray analyzer according to claim 1, wherein said controller further comprises fourth means for correcting the positional relationship between an irradiation position of said incident X-ray to said sample and said detector based on said obtained relationship, and said third means of said controller corrects an incident angle of said incident X-ray to said sample after ending the correction of said positional relationship.

4. The total reflection fluorescent X-ray analyzer according to claim 3, wherein said second means of said controller adjusts up and down positions of said sample base based on said obtained relationship so as to correct said positional relationship.

5. The total reflection fluorescent X-ray analyzer according to claim 1, wherein said second means of said controller obtains said standard value by dividing intensity of said scattered X-ray by intensity of said fluorescent X-ray.

6. The total reflection fluorescent X-ray analyzer according to claim 1, wherein said third means of said controller obtains a total reflection critical angle of said incident X-ray based on said obtained relationship, and corrects the incident angle of said incident X-ray to said sample based on the total reflection critical angle.

7. The total reflection fluorescent X-ray analyzer according to claim 1, wherein said controller further comprises fifth means for analyzing said sample after correcting the incident angle of said incident X-ray to the sample.

8. A method for analyzing a total reflection fluorescent X-ray comprising the steps of:

sequentially changing an incident angle of an incident X-ray to a sample to detect a fluorescent X-ray generated from said sample at each incident angle, and a scattered X-ray of said incident X-ray;

obtaining the relationship between the incident angle of said incident X-ray to said sample and a standard value obtained by standardizing intensity of said fluorescent X-ray by intensity of said scattered X-ray; and correcting a shift of the incident angle of said incident x-ray to said sample, and a shift of the irradiation position of said incident X-ray based on said obtained relationship, respectively.

9. The method according to claim 8, wherein the shift of the incident angle of said incident X-ray to said sample is corrected after correcting the shift of the irradiation position of said incident X-ray.

10. The method according to claim 8, wherein said standard value is obtained by dividing intensity of said scattered X-ray by intensity of said fluorescent X-ray.

11. The method according to claim 8, wherein the shift of the incident angle of said incident X-ray to said sample by obtaining a total reflection critical angle of said incident X-ray based on said obtained relationship, and obtaining a correct incident angle based on said total reflection critical angle.

* * * * *